United States Patent
Park et al.

(10) Patent No.: US 11,254,759 B2
(45) Date of Patent: Feb. 22, 2022

(54) TRANSITION METAL COMPOUND FOR OLEFIN POLYMERIZATION CATALYST, AND OLEFIN POLYMERIZATION CATALYST INCLUDING SAME

(71) Applicant: Hanwha Solutions Corporation, Seoul (KR)

(72) Inventors: Na Young Park, Daejeon (KR); Hyung Seung Lee, Daejeon (KR); Lan Hua Piao, Seoul (KR); Seong Yeon Park, Daejeon (KR); Wook Jeong, Daejeon (KR)

(73) Assignee: Hanwha Solutions Corporation, Seoul (KR)

( * ) Notice: Subject to any disclaimer, the term of this patent is extended or adjusted under 35 U.S.C. 154(b) by 33 days.

(21) Appl. No.: 16/770,301

(22) PCT Filed: Mar. 15, 2019

(86) PCT No.: PCT/KR2019/003018
§ 371 (c)(1),
(2) Date: Jun. 5, 2020

(87) PCT Pub. No.: WO2019/216541
PCT Pub. Date: Nov. 14, 2019

(65) Prior Publication Data
US 2020/0392260 A1    Dec. 17, 2020

(30) Foreign Application Priority Data

May 10, 2018 (KR) .................. 10-2018-0053513

(51) Int. Cl.
| | |
|---|---|
| *C07F 17/00* | (2006.01) |
| *C08F 4/6592* | (2006.01) |
| *C08F 4/642* | (2006.01) |
| *C08F 210/16* | (2006.01) |

(52) U.S. Cl.
CPC .......... *C08F 4/65927* (2013.01); *C07F 17/00* (2013.01); *C08F 4/642* (2013.01); *C08F 210/16* (2013.01)

(58) Field of Classification Search
CPC .... C07F 17/00; C08F 4/65927; C08F 210/16; C08L 23/0815
See application file for complete search history.

(56) References Cited

U.S. PATENT DOCUMENTS

| | | | |
|---|---|---|---|
| 7,238,818 | B2 | 7/2007 | Ewen et al. |
| 7,763,562 | B2 | 7/2010 | Voskoboynikov et al. |
| 9,481,747 | B2 | 11/2016 | Park et al. |
| 9,828,403 | B2 | 11/2017 | Lee et al. |
| 2002/0147104 | A1 | 10/2002 | Tsai et al. |
| 2003/0139284 | A1 | 7/2003 | Tsai et al. |
| 2015/0051360 | A1 | 2/2015 | Praetorius et al. |
| 2015/0299351 | A1 | 10/2015 | Praetorius et al. |
| 2017/0130159 | A1 | 5/2017 | Dias et al. |

FOREIGN PATENT DOCUMENTS

| | | |
|---|---|---|
| KR | 20000053294 A | 8/2000 |
| KR | 20150034655 A | 4/2015 |
| KR | 20160019875 A | 2/2016 |
| KR | 20170021325 A | 2/2017 |

OTHER PUBLICATIONS

Korean Notice of Grant of Patent issued in Korean Patent Application No. 10-2018-0053513, dated Jul. 20, 2020, with translation, 4 pages.
International Search Report and Written Opinion for International Application No. PCT/KR2019/003018, dated Jul. 3, 2019, 10 pages.
Japanese Notice of Reasons for Refusal for Japanese Application No. 2020-563546, dated Dec. 14, 2012 with translation, 6 pages.

*Primary Examiner* — Caixia Lu
(74) *Attorney, Agent, or Firm* — RatnerPrestia

(57) ABSTRACT

The present invention relates to a transition metal compound for an olefin polymerization catalyst, the transition metal compound being represented by chemical formula 1. The description of chemical formula 1 is as defined in the specification.

13 Claims, No Drawings

TRANSITION METAL COMPOUND FOR OLEFIN POLYMERIZATION CATALYST, AND OLEFIN POLYMERIZATION CATALYST INCLUDING SAME

CROSS REFERENCE TO RELATED APPLICATIONS

This application is the U.S. National Phase Application of PCT/KR2019/003018, filed Mar. 15, 2019, which claims priority to Korean Patent Application No. 10-2018-0053513, filed May 10, 2018, the contents of such applications being incorporated herein by reference.

FIELD

The present invention relates to a transition metal compound for an olefin polymerization catalyst and an olefin polymerization catalyst comprising the same.

BACKGROUND

A metallocene catalyst, which is one of the catalysts used to polymerize olefins, is a compound, in which a ligand such as a cyclopentadienyl group (Cp), an indenyl group, and a cycloheptadienyl group is coordinate bonded to a transition metal or a transition metal halogen compound, and has a sandwich structure in its basic form.

The metallocene catalyst is a single-site catalyst composing a metallocene compound and a cocatalyst such as methylaluminoxane. Polymers polymerized with the metallocene catalyst have a narrow molecular weight distribution, a uniform distribution of the comonomer, and a copolymerization activity higher than that of the Ziegler-Natta catalyst.

However, since there are still many difficulties in commercial use, a manufacturing technique based on the development of a catalyst having high activity and high copolymerizability even at a high temperature of 100° C. or higher and economic efficiency is required.

SUMMARY

The problem to be solved by the present invention is to provide a transition metal compound for an olefin polymerization catalyst having a ligand of a novel structure and an olefin polymerization catalyst having high activity and steric specificity including the same.

However, these problems are exemplary, and the scope of the present invention is not limited thereby.

According to an embodiment of the present invention for solving the above problems, a transition metal compound for an olefin polymerization catalyst represented by the following chemical formula 1 is provided.

<chemical formula 1>

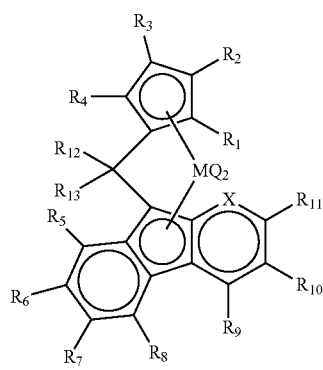

In the chemical formula 1, the M is any one of titanium (Ti), zirconium (Zr), and hafnium (Hf), the Q is each independently any one of halogen, a $C_{1-20}$ alkyl group, a $C_{2-20}$ alkenyl group, a $C_{2-20}$ alkynyl group, a $C_{6-20}$ aryl group, a $C_{1-20}$ alkyl $C_{6-20}$ aryl group, a $C_{6-20}$ aryl $C_{1-20}$ alkyl group, a $C_{1-20}$ alkylamido group, a $C_{6-20}$ arylamido group, and a $C_{1-20}$ alkylidene group, the X is nitrogen (N) or phosphorus (P), the $R_1$, $R_2$, $R_3$, $R_4$, $R_5$, $R_6$, $R_7$, $R_8$, $R_9$, $R_{10}$ and $R_{11}$ are each independently any one of hydrogen, a $C_{1-20}$ alkyl group, a $C_{2-20}$ alkenyl group, a $C_{2-20}$ alkynyl group, a $C_{6-20}$ aryl group, a $C_{1-20}$ alkyl $C_{6-20}$ aryl group, a $C_{6-20}$ aryl $C_{1-20}$ alkyl group, a $C_{1-20}$ alkylamido group, a $C_{6-20}$ arylamido group and a $C_{1-20}$ alkylidene group, the $R_{12}$ and $R_{13}$ are each independently any one of a $C_{1-20}$ alkyl group, a $C_{2-20}$ alkenyl group, a $C_{2-20}$ alkynyl group, a $C_{6-20}$ aryl group, a $C_{1-20}$ alkyl $C_{6-20}$ aryl group, a $C_{6-20}$ aryl $C_{1-20}$ alkyl group, a $C_{1-20}$ alkylamido group, a $C_{6-20}$ arylamido group and a $C_{1-20}$ alkylidene group, or may be linked to each other to form a substituted or unsubstituted $C_{4-20}$ ring.)

Specifically, the Q is each independently halogen or a $C_{1-20}$ alkylamido group, the $R_1$, $R_2$, $R_3$ and $R_4$ are each independently hydrogen, the $R_5$, $R_6$, $R_7$, $R_8$, $R_9$, $R_{10}$ and $R_{11}$ are each independently any one of hydrogen, a $C_{1-20}$ alkyl group, a phenyl group and a t-butyl group, the $R_{12}$ and $R_{13}$ are each independently a phenyl group or a $C_{1-20}$ alkyl group, or may be linked to each other to form a substituted or unsubstituted $C_{4-20}$ ring.

More specifically, the $R_{12}$ and $R_{13}$ are each independently a phenyl group or a methyl group or may be linked to each other to form an aliphatic $C_{4-6}$ ring.

Alternatively, the $R_5$, $R_6$, $R_7$, $R_8$, $R_9$, $R_{10}$ and $R_{11}$ may each independently be any one of hydrogen, a phenyl group, a methyl group and a t-butyl group.

For example, the chemical formula 1 may be represented by any one of the following chemical formulas 1-1 to 1-23.

<chemical formula 1-1>

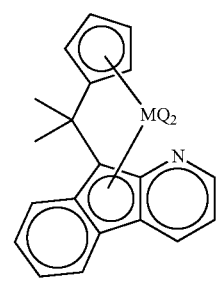

<chemical formula 1-2>

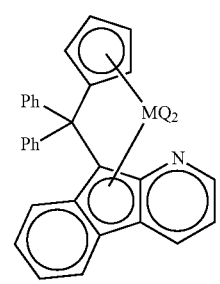

<chemical formula 1-3>
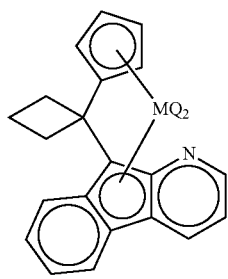
<chemical formula 1-4>
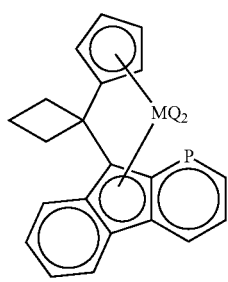
<chemical formula 1-5>
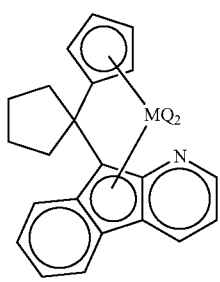
<chemical formula 1-6>
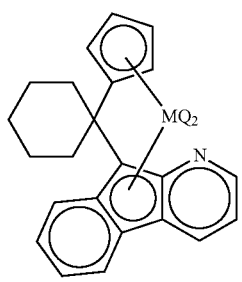
<chemical formula 1-7>
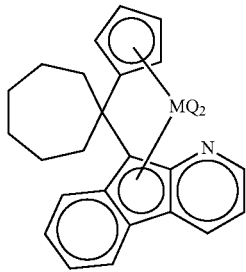
<chemical formula 1-8>
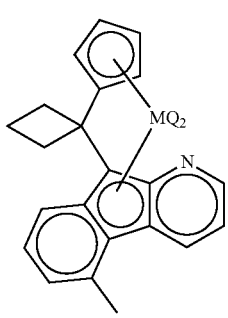
<chemical formula 1-9>
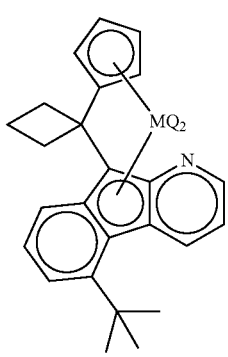
<chemical formula 1-10>
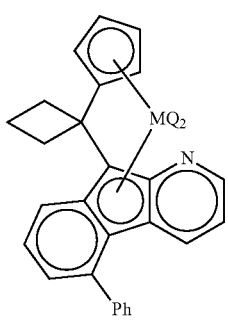
<chemical formula 1-11>
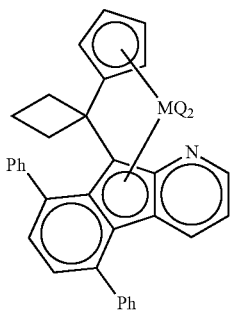
<chemical formula 1-12>
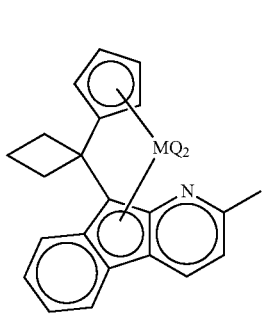

-continued
<chemical formula 1-13>
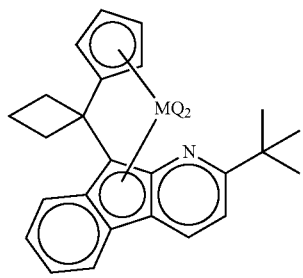
<chemical formula 1-14>
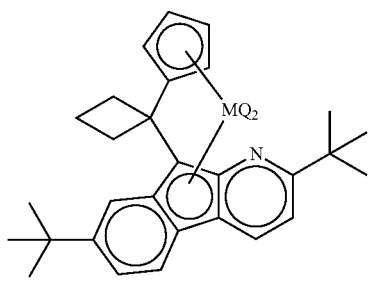
<chemical formula 1-15>
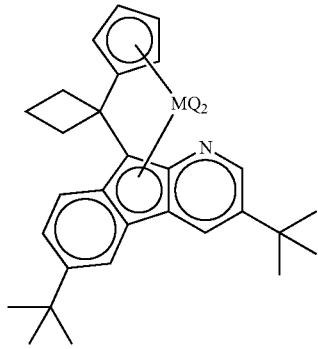
<chemical formula 1-16>
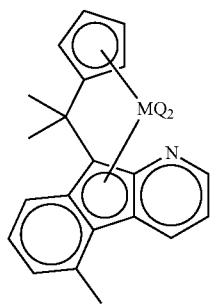
<chemical formula 1-17>
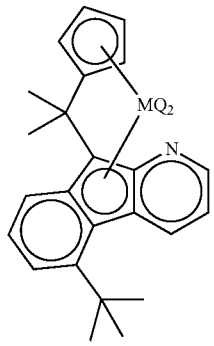
-continued
<chemical formula 1-18>
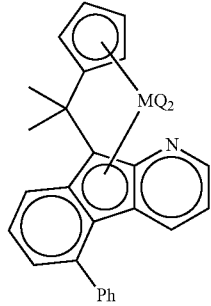
<chemical formula 1-19>
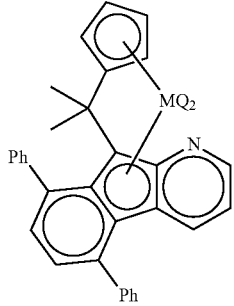
<chemical formula 1-20>
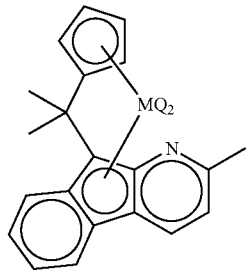
<chemical formula 1-21>
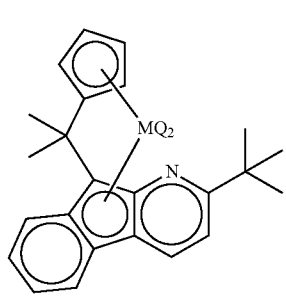
<chemical formula 1-22>
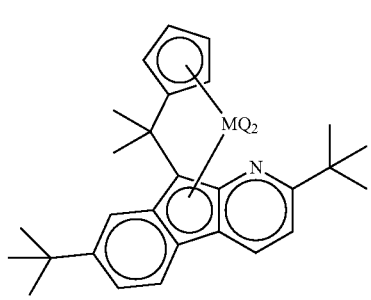

<chemical formula 1-23>

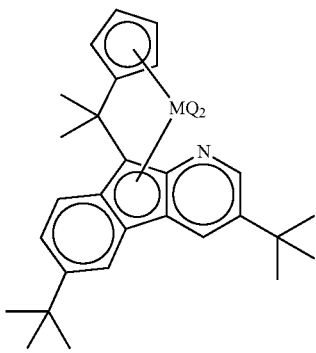

Further, according to another embodiment of the present invention for solving the above problems, an olefin polymerization catalyst may include a transition metal compound for an olefin polymerization catalyst represented by the following chemical formula 1 and a cocatalyst compound.

<chemical formula 1>

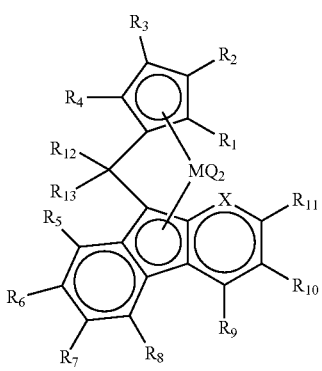

(In the chemical formula 1,
the M is any one of titanium (Ti), zirconium (Zr) and hafnium (Hf), the Q is each independently any one of halogen, a $C_{1-20}$ alkyl group, a $C_{2-20}$ alkenyl group, a $C_{2-20}$ alkynyl group, a $C_{6-20}$ aryl group, a $C_{1-20}$ alkyl $C_{6-20}$ aryl group, a $C_{6-20}$ aryl $C_{1-20}$ alkyl group, a $C_{1-20}$ alkylamido group, a $C_{6-20}$ arylamido group and a $C_{1-20}$ alkylidene group, the X is nitrogen (N) or phosphorus (P), the $R_1$, $R_2$, $R_3$, $R_4$, $R_5$, $R_6$, $R_7$, $R_8$, $R_9$, $R_{10}$ and $R_{11}$ are each independently any one of hydrogen, a $C_{1-20}$ alkyl group, a $C_{2-20}$ alkenyl group, a $C_{2-20}$ alkynyl group, a $C_{6-20}$ aryl group, a $C_{1-20}$ alkyl $C_{6-20}$ aryl group, a $C_{6-20}$ aryl $C_{1-20}$ alkyl group, a $C_{1-20}$ alkylamido group, a $C_{6-20}$ arylamido group and a $C_{1-20}$ alkylidene group, and the $R_{12}$ and $R_{13}$ are each independently any one of a $C_{1-20}$ alkyl group, $C_{2-20}$ alkenyl group, a $C_{2-20}$ alkynyl group, a $C_{6-20}$ aryl group, a $C_{1-20}$ alkyl $C_{6-20}$ aryl group, a $C_{6-20}$ aryl $C_{1-20}$ alkyl group, a $C_{1-20}$ alkylamido group, a $C_{6-20}$ arylamido group and a $C_{1-20}$ alkylidene group, or may be linked to each other to form a substituted or unsubstituted $C_{4-20}$ ring.)

Here, the Q is each independently halogen or a $C_{1-20}$ alkylamido group, the $R_1$, $R_2$, $R_3$ and $R_4$ are each independently hydrogen, the $R_5$, $R_6$, $R_7$, $R_8$, $R_9$, $R_{10}$ and $R_{11}$ are each independently any one of hydrogen, a $C_{1-20}$ alkyl group, a phenyl group and a t-butyl group, and the $R_{12}$ and $R_{13}$ are each independently a phenyl group or a $C_{1-20}$ alkyl group, or may be linked to each other to form a substituted or unsubstituted $C_{4-20}$ ring.

Specifically, the chemical formula 1 may be represented by any one of chemical formulas 1-1 to 1-23 below.

<chemical formula 1-1>

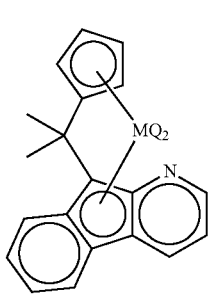

<chemical formula 1-2>

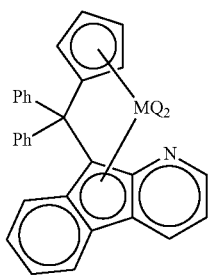

<chemical formula 1-3>

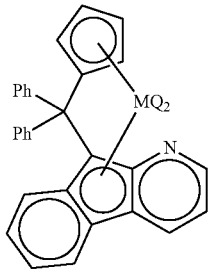

<chemical formula 1-4>

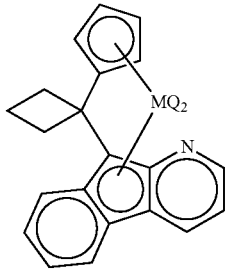

<chemical formula 1-5>

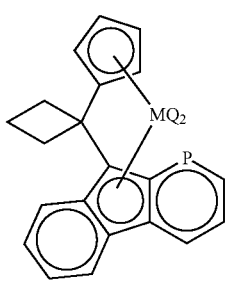

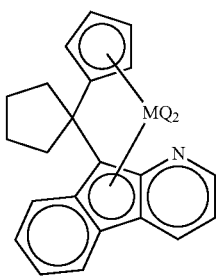

<chemical formula 1-6>
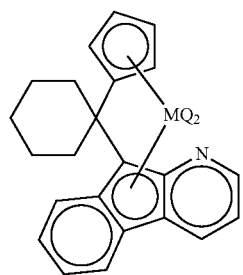
<chemical formula 1-7>
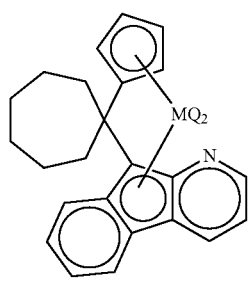
<chemical formula 1-8>
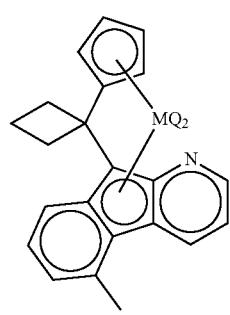
<chemical formula 1-9>
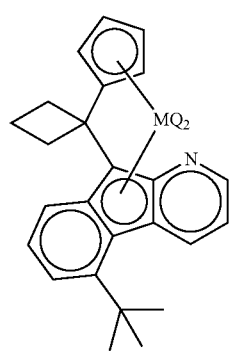
<chemical formula 1-10>
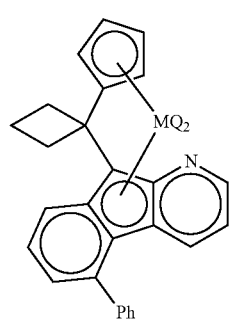
<chemical formula 1-11>
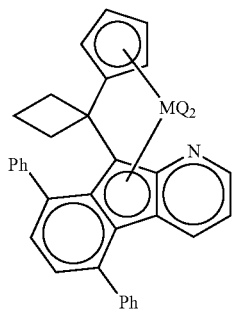
<chemical formula 1-12>
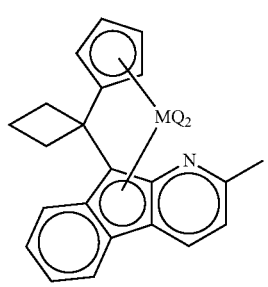
<chemical formula 1-13>
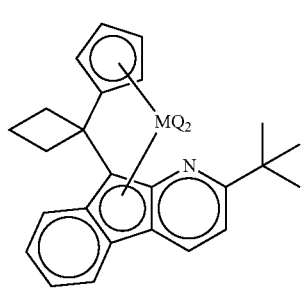
<chemical formula 1-14>
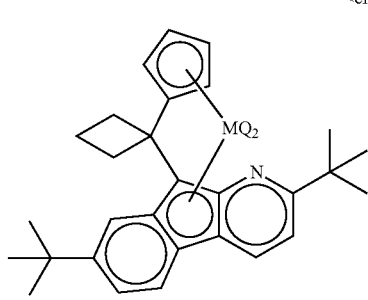
<chemical formula 1-15>
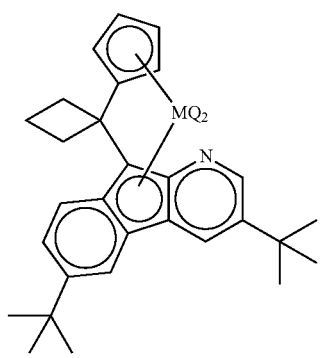

<chemical formula 1-16>

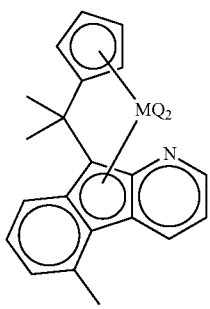

<chemical formula 1-17>

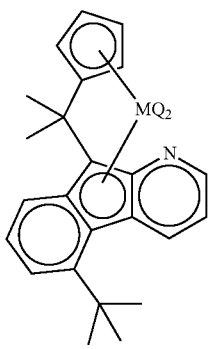

<chemical formula 1-18>

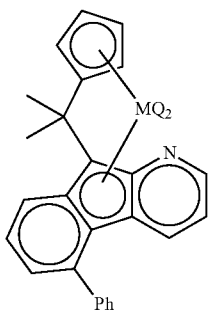

<chemical formula 1-19>

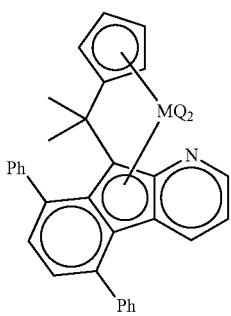

<chemical formula 1-20>

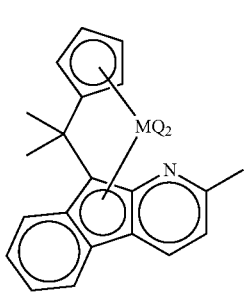

<chemical formula 1-21>

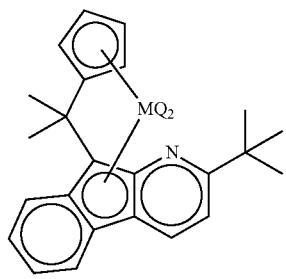

<chemical formula 1-22>

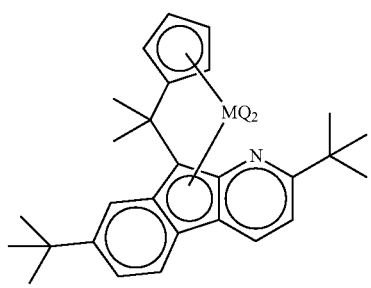

<chemical formula 1-23>

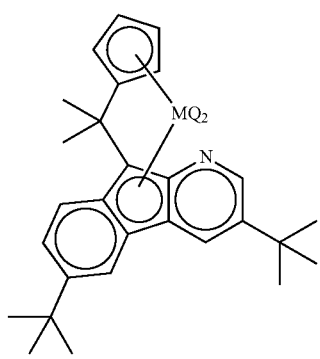

Further, the cocatalyst compound may include at least one of compounds represented by the following chemical formulas 2 to 4.

<chemical formula 2>

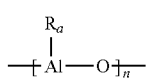

(In the chemical formula 2, n is an integer of 2 or more, and $R_a$ may be a halogen atom, a $C_{1-20}$ hydrocarbon group, or a $C_{1-20}$ hydrocarbon group substituted with halogen.)

<chemical formula 3>

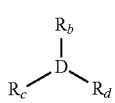

(In the chemical formula 3, D is aluminum (Al) or boron (B), and $R_b$, $R_c$ and $R_d$ may each independently be a halogen atom, a $C_{1-20}$ hydrocarbon group, a $C_{1-20}$ hydrocarbon group substituted with halogen or a $C_{1-20}$ alkoxy group.)

$[L\text{-}H]^+[Z(A)_4]^-$ or $[L]^+[Z(A)_4]^-$     <chemical formula 4>

(In the chemical formula 4, L is a neutral or cationic Lewis base, $[L\text{-}H]^+$ and $[L]^+$ are Brønsted acids, Z is a group 13 element, and A may each independently be a substituted or unsubstituted $C_{6-20}$ aryl group or a substituted or unsubstituted $C_{1-20}$ alkyl group.)

According to one embodiment, an olefin polymerization catalyst having high activity and steric specificity may be prepared by comprising the transition metal compound of the present invention.

Further, the olefin polymerization catalyst comprising the transition metal compound according to an embodiment of the present invention has a high synthetic yield and can be easily prepared by an economical method, and thus has excellent commercial practicality.

The effects according to the embodiments of the present invention are not limited by the contents illustrated above, and more various effects are included in the present specification.

DETAILED DESCRIPTION

Advantages and features of the present invention, and a method of achieving them will be clarified with reference to embodiments described below in detail. However, the present invention is not limited to the embodiments disclosed below, but will be implemented in various different forms, and the present embodiments are only provided to allow the disclosure of the present invention to be complete, and fully inform the ordinary knowledge in the technical field to which the present invention pertains on the scope of the invention, and the invention is only defined by the scope of the claims.

Although the first, second, etc. are used to describe various components, these components are not limited by these terms. These terms are only used to distinguish one component from another component.

In this specification, the term "$C_{A-B}$" means "the number of carbon is A or more and B or less", and the terms "A to B" mean "A or more and B or less," and in the term "substituted or unsubstituted," "substituted" means that "at least one hydrogen of a hydrocarbon compound or hydrocarbon derivative is substituted with halogen, $C_{1-20}$ alkyl, $C_{2-20}$ alkenyl, $C_{2-20}$ alkynyl, $C_{6-20}$ aryl, $C_{1-20}$ alkyl $C_{6-20}$ aryl, $C_{6-20}$ aryl $C_{1-20}$ alkyl, $C_{1-20}$ alkylamido, $C_{6-20}$ arylamido or $C_{1-20}$ alkylidene," and "unsubstituted" means "at least one hydrogen of a hydrocarbon compound or hydrocarbon derivative is unsubstituted with halogen, $C_{1-20}$ alkyl, $C_{2-20}$ alkenyl, $C_{2-20}$ alkynyl, $C_{6-20}$ aryl, $C_{1-20}$ alkyl $C_{6-20}$ aryl, $C_{6-20}$ aryl $C_{1-20}$ alkyl, $C_{1-20}$ alkylamido, $C_{6-20}$ arylamido or $C_{1-20}$ alkylidene."

The present invention relates to a transition metal compound for an olefin polymerization catalyst having a novel ligand structure. The olefin polymerization catalyst comprising the transition metal compound may have high activity and a stereospecific structure.

First, the transition metal compound for an olefin polymerization catalyst according to an embodiment of the present invention may be represented by the following chemical structure formula 1.

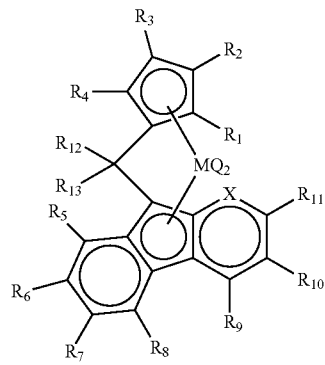

<chemical formula 1>

In the chemical formula 1, the M may be any one of titanium (Ti), zirconium (Zr) and hafnium (Hf). For example, M may be zirconium or hafnium.

The Q may each independently be any one of halogen, a $C_{1-20}$ alkyl group, a $C_{2-20}$ alkenyl group, a $C_{2-20}$ alkynyl group, a $C_{6-20}$ aryl group, a $C_{1-20}$ alkyl $C_{6-20}$ aryl group, a $C_{6-20}$ aryl $C_{1-20}$ alkyl group, a $C_{1-20}$ alkylamido group, a $C_{6-20}$ arylamido group and a $C_{1-20}$ alkylidene group. More specifically, Q may each independently be a N,N'-Methylamido group (NMe$_2$) or a N,N'-Ethylamido group (NEt$_2$).

The $R_1$, $R_2$, $R_3$, $R_4$, $R_5$, $R_6$, $R_7$, $R_8$, $R_9$, $R_{10}$ and $R_{11}$ may each independently be any one of hydrogen, a $C_{1-20}$ alkyl group, a $C_{2-20}$ alkenyl group, a $C_{2-20}$ alkynyl group, a $C_{6-20}$ aryl group, a $C_{1-20}$ alkyl $C_{6-20}$ aryl group, a $C_{6-20}$ aryl $C_{1-20}$ alkyl group, a $C_{1-20}$ alkylamido group, a $C_{6-20}$ arylamido group and a $C_{1-20}$ alkylidene group. Specifically, $R_1$, $R_2$, $R_3$ and $R_4$ are each independently hydrogen, and $R_5$, $R_6$, $R_7$, $R_8$, $R_9$, $R_{10}$ and $R_{11}$ may each independently be hydrogen, a $C_{1-20}$ alkyl group or a $C_{6-20}$ aryl group. More specifically, $R_1$, $R_2$, $R_3$ and $R_4$ are each independently hydrogen, and $R_5$, $R_6$, $R_7$, $R_8$, $R_9$, $R_{10}$ and $R_{11}$ may each independently be any one of hydrogen, a methyl group, a phenyl group and a t-butyl group.

The $R_{12}$ and $R_{13}$ are each independently a $C_{1-20}$ alkyl group, a $C_{2-20}$ alkenyl group, a $C_{2-20}$ alkynyl group, a $C_{6-20}$ aryl group, a $C_{1-20}$ alkyl $C_{6-20}$ aryl group, a $C_{6-20}$ aryl $C_{1-20}$ alkyl group, a $C_{1-20}$ alkylamido group, a $C_{6-20}$ arylamido group, and a $C_{1-20}$ alkylidene group, or may be linked to each other to form a substituted or unsubstituted $C_{4-20}$ ring. Specifically, $R_{12}$ and $R_{13}$ may be a $C_{1-20}$ alkyl group or a $C_{6-20}$ aryl group, or may be linked to each other to form a substituted or unsubstituted $C_{4-20}$ ring. More specifically, $R_{12}$ and $R_{13}$ are a methyl group or a phenyl group, or may be linked to each other to form a substituted or unsubstituted $C_{4-6}$ ring.

The X may be nitrogen (N) or phosphorus (P). The transition metal compound for an olefin polymerization catalyst represented by chemical formula 1 has the ligand structure having a fluorene structure, in which carbon number 1 ($C_1$) of fluorene is substituted with a hetero atom such as nitrogen (N) or phosphorus (P). The ligand structure comprising the hetero atom may differently control the electrical and steric environment around the catalyst center metal (M) than the structure comprising only carbon.

For example, a hetero atom having a greater electronegativity than carbon and having a non-bonding electron pair can further stabilize the metal by providing electrons to the catalyst center metal of the ligand structure. The catalyst center metal stabilized by the hetero atom may have high activity as an olefin polymerization catalyst.

Further, the transition metal compound for an olefin polymerization catalyst may have a specific steric conformation by a hetero atom. Unlike carbon, hetero atoms have a non-bonding electron in the fluorene group rather than hydrogen (H). When carbon number 1 of fluorene is substituted with a hetero atom, a region having a high electron density may be formed by a non-bonding electron pair between the catalyst center metal and the hetero atom. Due to this, the olefin monomer has limited access to the region between the hetero atom and the catalyst center metal, and specific access to a region having a small steric effect other than the above region may be possible. Therefore, when the olefin monomer is polymerized, the prepared olefin polymer may exhibit specific steric properties because it reacts with the transition metal compound for the olefin polymerization catalyst at a specific position.

The transition metal compound for an olefin polymerization catalyst of the present invention can have high activity as a catalyst because the catalyst center metal can be stabilized by receiving electrons through a non-bonding electron pair of a hetero atom. Further, the transition metal compound for the olefin polymerization catalyst can form a region having a high electron density between the catalyst center metals by a non-bonding electron pair of the hetero atom. Therefore, when the olefin monomer is approached, a structure that induces a specific approach to only a region having a small steric effect may be obtained, and the prepared olefin polymer may have a steric specific structure.

The hetero atom can be nitrogen (N) or phosphorus (P). Nitrogen and phosphorus are elements located in group 15 of the periodic table, and unlike an element in other groups, they can have a non-bonding electron pair without charge even if they are substituted with carbon number 1 ($C_1$) of fluorene. Through this, electrons may be provided to the catalyst center metal. Further, since nitrogen and phosphorus are elements corresponding to cycles 2 and 3, respectively, even when substituted with a fluorene structure, they have an atomic size that does not interfere with access of the olefin monomer. If the size of the atom is too large, the steric effect may interfere with the approach of the olefin monomer. On the other hand, in the case of nitrogen or phosphorus, it has an appropriate atom size such that it does not interfere with the access of the olefin monomer while forming a region with a small steric effect through interaction with the catalyst center metal. Therefore, the transition metal compound for an olefin polymerization catalyst including a fluorene group substituted with nitrogen or phosphorus may have a steric structure, in which the specific approach of an olefin monomer is possible.

In an exemplary embodiment, the transition metal compound for an olefin polymerization catalyst of the present invention may be represented by any one of the following chemical formulas 1-1 to 1-23.

<chemical formula 1-1>

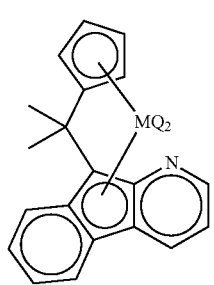

<chemical formula 1-2>

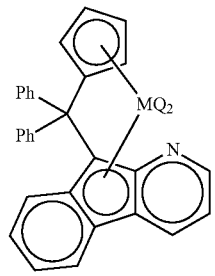

<chemical formula 1-3>

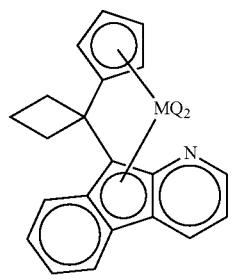

<chemical formula 1-4>

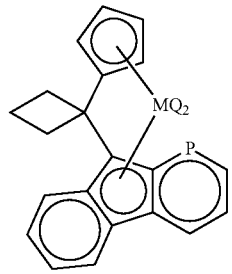

<chemical formula 1-5>

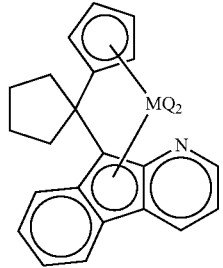

<chemical formula 1-6>

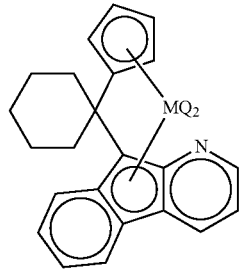

<chemical formula 1-7>
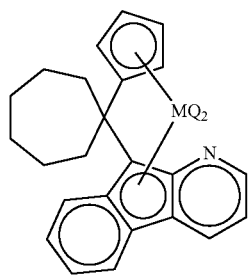
<chemical formula 1-8>
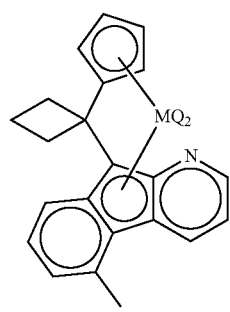
<chemical formula 1-9>
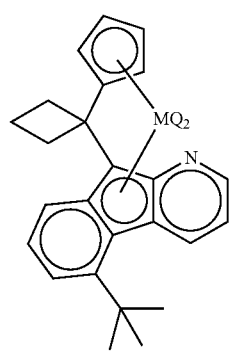
<chemical formula 1-10>
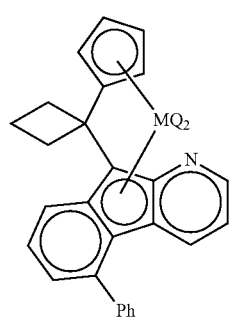
<chemical formula 1-11>
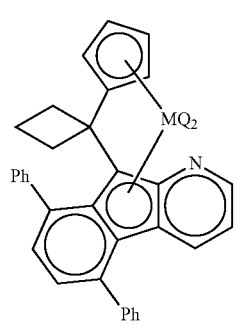
<chemical formula 1-12>
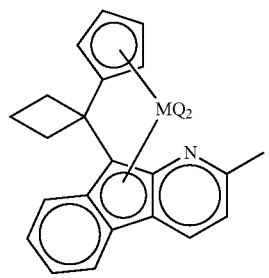
<chemical formula 1-13>
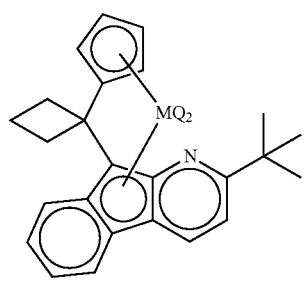
<chemical formula 1-14>
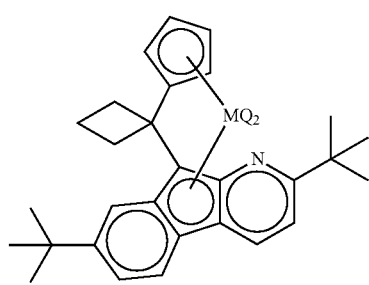
<chemical formula 1-15>
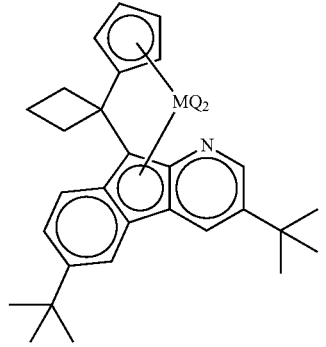
<chemical formula 1-16>
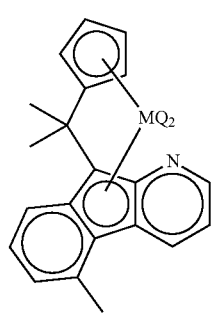

<chemical formula 1-17>

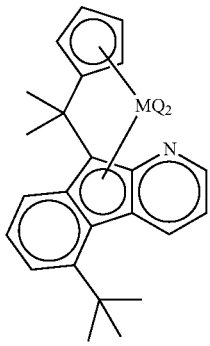

<chemical formula 1-18>

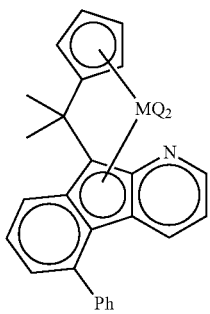

<chemical formula 1-19>

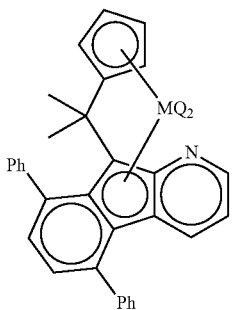

<chemical formula 1-20>

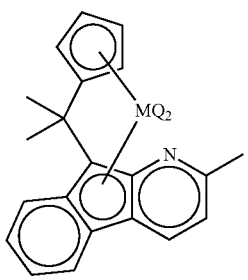

<chemical formula 1-21>

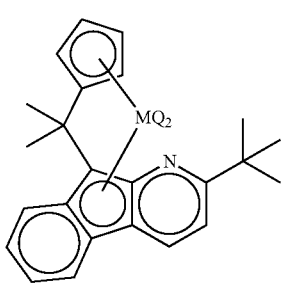

<chemical formula 1-22>

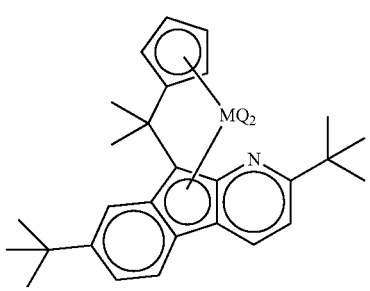

<chemical formula 1-23>

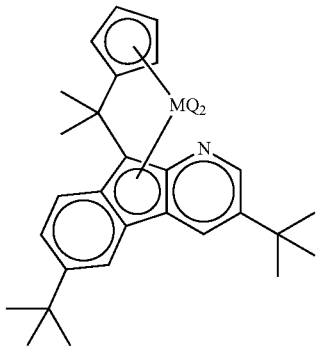

The transition metal compound for an olefin polymerization catalyst of the present invention described above may be synthesized by reacting a precursor of nitrogen or phosphorus with an aromatic compound.

As an example of a method for synthesizing fluorine, in which carbon number 1 is substituted with a hetero atom, the transition metal compound for an olefin polymerization catalyst may be prepared by reacting a precursor comprising nitrogen or phosphorus from an indanone or a derivative thereof as a starting material. Here, the indanone derivative may have a structure, in which hydrogen or an alkyl group having 1 to 6 carbon atoms or an aryl group is bonded to carbon positions 4 to 7 of the indanone. And, as a precursor comprising nitrogen or phosphorus, a precursor, in which an amine group or a phospho group or the like is combined with an alkyne group having 3 to 7 carbon atoms may be used. In an embodiment, the precursor comprising nitrogen may be Propargylamine, and the precursor comprising phosphorus may be Propargylphosphine. However, it is not limited thereto, and the structure of the precursor comprising nitrogen or phosphorus may be changed according to the structure of the substituent of fluorene.

As another example, the transition metal compound for the olefin polymerization catalyst may be prepared through dehydrocyclization. In an embodiment, it can also be prepared through dehydrocyclization with a 2-methyl-3-phenylpyridine derivative or a 2-methyl-3-phenylphosphorine derivative as a starting material. However, the present invention is not limited thereto.

On the other hand, according to an embodiment of the present invention, the olefin polymerization catalyst may include any one of the transition metal compounds for the olefin polymerization catalyst described above and a cocatalyst compound.

The cocatalyst compound may include at least any one of compounds represented by the following chemical formulas 2 to 4.

<chemical formula 2>

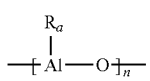

In the chemical formula 2, n may be an integer of 2 or more, and $R_a$ may be a halogen atom, a $C_{1-20}$ hydrocarbon group, or a $C_{1-20}$ hydrocarbon group substituted with halogen. For example, $R_a$ may be methyl, ethyl, n-butyl or isobutyl, but the present invention is not limited thereto.

<chemical formula 3>

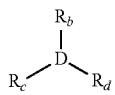

In the chemical formula 3, D is aluminum (Al) or boron (B), and $R_b$, $R_c$, and $R_d$ may each independently be a halogen atom, a $C_{1-20}$ hydrocarbon group, a $C_{1-20}$ hydrocarbon group substituted with halogen, or a $C_{1-20}$ alkoxy group. For example, when D is aluminum, the $R_b$, $R_c$ and $R_d$ may each independently be methyl or isobutyl, and when the D is boron, $R_b$, $R_c$ and $R_d$ may each be pentafluorophenyl, but the present invention is not limited thereto.

$$[L-H]^+[Z(A)_4]^- \text{ or } [L]^+[Z(A)_4]^- \quad \text{<chemical formula 4>}$$

In the chemical formula 4, L is a neutral or cationic Lewis base, $[L-H]^+$ and $[L]^+$ are Brønsted acids, Z is a group 13 element, and A may each independently be a substituted or unsubstituted $C_{6-20}$ aryl group or a substituted or unsubstituted $C_{1-20}$ alkyl group. For example, the $[L-H]^+$ may be a dimethylanilinium cation, $[Z(A)4]^-$ may be $[B(C_6F_5)_4]^-$, and $[L]^+$ may be $[(C_6H_5)_3C]^+$, but the present invention is not limited thereto.

Meanwhile, the olefin polymerization catalyst may further include a carrier.

The carrier is not particularly limited as long as it can carry a transition metal compound for an olefin polymerization catalyst and a cocatalyst compound. In an exemplary embodiment, the carrier may be carbon, silica, alumina ($Al_2O_3$), zeolite, magnesium chloride ($MgCl_2$), or the like.

As a method of carrying the transition metal compound for the olefin polymerization catalyst and the cocatalyst compound on the carrier, a physical adsorption method or a chemical adsorption method can be used. For example, the physical adsorption method may be a method, in which a solution of dissolving a transition metal compound for a olefin polymerization catalyst is contacted with a carrier and then dried, a method, in which a solution of dissolving a transition metal compound for a olefin polymerization catalyst and a cocatalyst compound is contacted with a carrier and then dried, or a method, in which a solution of dissolving a transition metal compound for an olefin polymerization catalyst is contacted with a carrier and then dried, and a carrier carrying a transition metal compound for an olefin polymerization catalyst is prepared, and separately, a solution of dissolving a cocatalyst compound is contacted with a carrier and then dried to prepare a carrier carrying the cocatalyst compound, and then mixing them.

Further, the chemical adsorption method may be a method of first carrying a cocatalyst compound on a surface of a carrier, and carrying a transition metal compound for an olefin polymerization catalyst in a cocatalyst compound, or a method of covalently bonding a functional group on the surface of the carrier (e.g., a hydroxy group (—OH) on the silica surface in the case of silica) with a catalyst compound.

Meanwhile, the total amount of the carrying amount of the main catalyst compound including the transition metal compound may be 0.001 mmol to 1 mmol based on 1 g of the carrier, and the carrying amount of the cocatalyst compound may be 2 mmol to 15 mmol based on the 1 g of the carrier.

However, such a carrier is not necessarily included, and whether or not to use it can be appropriately selected as necessary.

Further, the polyolefin may be formed by polymerizing the olefin-based monomer under the olefin polymerization catalyst according to an embodiment of the present invention.

The polyolefin may be, for example, a homopolymer or a copolymer polymerized by polymerization reactions such as free radical, cationic, coordination, condensation and addition, but the present invention is not limited thereto.

Meanwhile, the polyolefin may be prepared by gas phase polymerization, solution polymerization or slurry polymerization. Examples of the solvent that can be used when the polyolefin is prepared by solution polymerization or slurry polymerization include $C_{5-12}$ aliphatic hydrocarbon solvents such as pentane, hexane, heptane, nonane, decane and isomers thereof; aromatic hydrocarbon solvents such as toluene and benzene; hydrocarbon solvents substituted with chlorine atoms such as dichloromethane and chlorobenzene; and mixtures of them, and the like, but the present invention is not limited thereto.

Here, the olefin-based monomer may be one or more selected from the group comprising $C_{2-20}$ α-olefin, $C_{1-20}$ diolefin, $C_{3-20}$ cyclo-olefin and $C_{3-20}$ cyclo-diolefin.

For example, the olefin-based monomer may be ethylene, propylene, 1-butene, 1-pentene, 4-methyl-1-pentene, 1-hexene, 1-heptene, 1-octene, 1-decene, 1-undecene, 1-dodecene, 1-tetradecene, and 1-hexadecene, and the like, and the polyolefin may be a homopolymer comprising only one of the olefin-based monomers illustrated above or a copolymer comprising two or more. Preferably, the polyolefin may be a copolymer, in which ethylene and 1-octene are copolymerized, but is not limited thereto.

Hereinafter, a specific preparation example of the transition metal compound for an olefin polymerization catalyst of the present invention will be described.

<Preparation Example 1> Preparation of a Compound of Chemical Formula A

First, according to the following chemical reaction formula 1, a compound of chemical formula A (5) is prepared.

[chemical reaction formula 1]

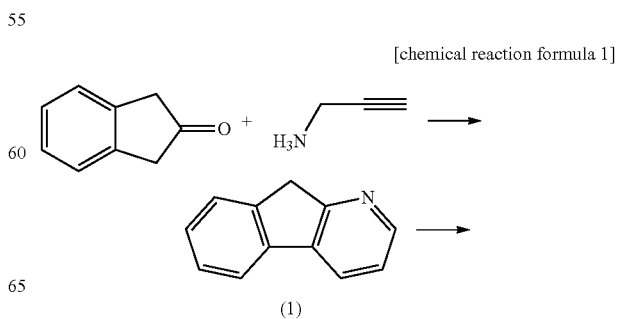

(1)

-continued

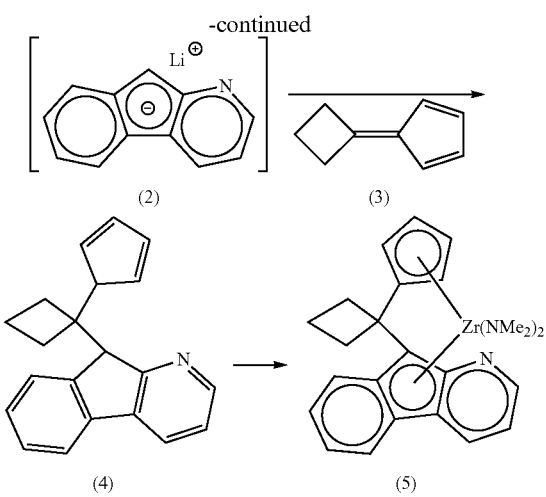

Preparation Example 1-1: Preparation of 9H-Indeno[2,1-b]pyridine (1)

A solution of propargylamine (2.42 g, 44 mmol) diluted in ethanol (5 mL) is added at 0° C. to a solution of 2-Indanone (5.0 g, 38 mmol) and sodium tetrachloroaurate (III) dihydrate (301 mg, 2 mol %) diluted in ethanol (45 mL). Then, after gradually raising the temperature to room temperature, the mixture is stirred under reflux at 78° C. for 1 hour. After the reaction is completed, ethanol is removed under vacuum, and then 3.27 g (52%) of a black liquid compound having the following $^1$H-NMR spectrum was obtained through column chromatography (hexane:ethyl acetate=5:1, v/v).

$^1$H-NMR (CDCl3, 300 MHz): δ 8.47 (dd, 1H), 7.99 (dd, 1H), 7.77 (dd, 1H), 7.58-7.56 (m, 1H), 7.41-7.32 (m, 2H), 7.25 (dd, 1H), 4.00 (s, 2H).

Preparation Example 1-2: Preparation of (9H-Indeno[2,1-b]pyridin-9-yl)lithium (2)

n-BuLi (4.19 g, 9.9 mmol, 1.6 M in hexane) is slowly added at −30° C. to a solution, in which 9-H-indeno[2,1-b]pyridine (1.50 g, 9.0 mmol) (1) prepared in the preparation example 1-1 was diluted in diethyl ether (50 mL), and the temperature is gradually raised to room temperature and stirred for 12 hours. The resulting solid was then filtered and dried under vacuum to obtain 1.63 g (100%) of a red solid compound.

Preparation Example 1-3: Preparation of 5-Cyclobutylidene-1,3-cyclopentadiene (3)

To a solution of Sodium cyclopentadienylide (80.30 g, 171 mmol, 2.0 M in THF) diluted in methanol (120 mL), a solution of cyclobutanone (6.00 g, 86 mmol) diluted in methanol (20 mL) and a solution of pyrrolidine (12.18 g, 171 mmol) diluted in methanol (20 mL) are slowly added in order at 0° C., and the temperature is gradually raised to room temperature and stirred for 12 hours. After completion of the reaction, the mixture is neutralized with 10% HCl aqueous solution, and extracted with pentane to separate the organic layer. Then, after removing the remaining water with MgSO$_4$, all solvents are removed under vacuum to obtain 1.62 g (16%) of a yellow oil compound having the following $^1$H-NMR spectrum.

$^1$H-NMR (CDCl3, 300 MHz): δ 6.45-6.43 (m, 2H), 6.30-6.28 (d, 2H), 3.13 (t, 4H), 2.22-2.12 (m, 2H).

Preparation Example 1-4: Preparation of 9-[(2,4-Cyclopentadienyl)-1-cyclobutyl]-indeno [2,1-b] pyridine (4)

A solution, in which (9H-indeno[2,1-b]pyridin-9-yl) lithium (1.50 g, 8.66 mmol) (2) prepared in the preparation example 1-2 diluted in THF (15 mL) is slowly dropped at −78° C. to a solution, in which 5-cyclobutylidene-1,3-cyclopentadiene (1.54 g, 13.0 mmol) (3) prepared in the preparation example 1-3 is diluted in THF (8 mL), and the temperature is gradually raised to room temperature and stirred for 12 hours. Then, the reaction was terminated by adding distilled water at 0° C., and extracted with dichloromethane to separate the organic layer. After removing the remaining water with MgSO$_4$, column chromatography (hexane:ethyl acetate=10:1, v/v) separates it to obtain 1.65 g (67%) of a light brown solid compound having the following $^1$H-NMR spectrum.

$^1$H-NMR (CDCl3, 300 MHz): δ 8.46 (m, 1H), 7.82-7.76 (m, 1H), 7.60-7.54 (m, 1H), 7.45 (d, 1H), 7.33-7.15 (m, 3H)), 6.12-5.63 (m, 3H), 4.29 (d, 1H), 3.10-2.99 (m, 1H), 2.85-2.68 (m, 1H), 2.60 (s, 1H), 2.43-2.36 (m, 2H)), 2.21 (d, 1H), 1.99-1.88 (d, 2H).

Preparation Example 1-5: Preparation of cyclobutylidene[(cyclopentadienyl)-(indeno[2,1-b]pyridinyl)]zirconium bis(dimethylamido) (5)

A solution of tetrakis(dimethylamido)zirconium (IV) (141 mg, 0.52 mmol) diluted in toluene (1 mL) is slowly added at −30° C. to a solution, in which 9-[(2,4-cyclopentadienyl)-1-cyclobutyl]-indeno[2,1-b]pyridine (150 mg, 0.52 mmol) (4) prepared in the preparation example 1-4 is diluted in toluene (1.5 mL), and the temperature is gradually raised to room temperature and stirred for 12 hours. And after drying it under vacuum to remove the reaction solvent and by-products, it is washed with hexane to obtain 235 mg (97%) of the ultramarine solid compound having the following $^1$H-NMR spectrum, which is represented by chemical formula A (5).

$^1$H-NMR (benzene-d6, 300 MHz): δ 8.48 (d, 1H), 8.34 (d, 1H), 8.03 (d, 1H), 7.94 (d, 1H), 7.72 (t, 1H), 7.41 (t, 1H), 6.22 (t, 1H), 6.03 (t, 2H), 5.85 (t, 2H), 3.78 (q, 2H), 2.63 (s, 12H), 2.41-2.38 (m, 2H), 2.22-2.17 (m, 2H).

<chemical formula A>

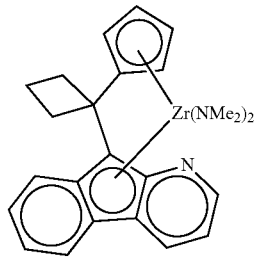

<Preparation Example 2> Preparation of a Compound of the Chemical Formula B

Using the compound (4) prepared in the preparation example 1-4, a compound of chemical formula B (6) is prepared according to the following chemical reaction formula 2.

[chemical reaction formula 2]

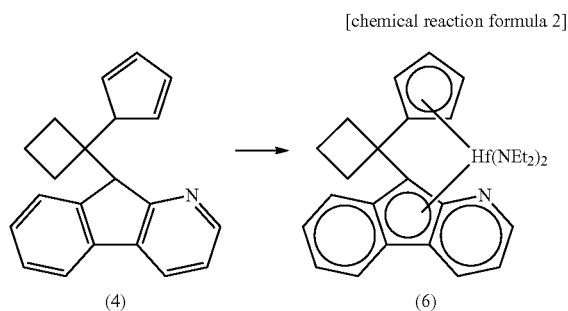

Preparation Example 2-1: Preparation of cyclobutylidene[(cyclopentadienyl)-(indeno[2,1-b]pyridinyl)]hafnium bis(diethylamido) (6)

A solution of tetrakis(diethylamido)hafnium(IV) (190 mg, 0.37 mmol) diluted in toluene (1 mL) is slowly added at −30° C. to a solution, in which 9-[(2,4-cyclopentadienyl)-1-cyclobutyl]-indeno[2,1-b]pyridine (100 mg, 0.35 mmol) (4) prepared in the preparation example 1-4 is diluted in toluene (2 mL), and the temperature is gradually raised to room temperature, and then stirred at 130° C. for 12 hours. And after drying under vacuum to remove the reaction solvent and by-products, it is washed with hexane to obtain 108 mg (46%) of the ultramarine solid compound having the following $^1$H-NMR spectrum, which is represented by chemical structure formula B (6).

$^1$H-NMR (benzene-d6, 300 MHz): δ 8.49 (d, 1H), 8.32 (d, 1H), 8.10 (d, 1H), 7.98 (d, 1H), 7.73 (t, 1H), 7.42 (t, 1H), 6.22 (t, 1H), 6.08 (t, 2H), 5.94 (t, 2H), 3.81 (q, 2H), 3.26-3.17 (m, 4H), 3.12-3.01 (m, 4H), 2.50-2.42 (m, 2H), 2.28-2.13 (m, 2H), 0.79 (t, 12H).

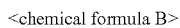

<chemical formula B>

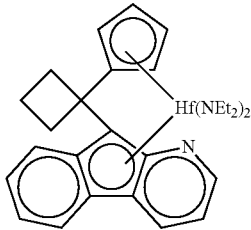

Chemical formulas A and B prepared through the above method have a structure, in which carbon number 1 of the fluorene group is substituted with nitrogen as described above. The nitrogen atom can provide electrons through a non-bonding electron pair to zirconium (Zr) or hafnium (Hf), which is the catalyst center metal, and allow chemical formulas A and B to have a specific steric conformation. Through this, zirconium or hafnium, which is the catalyst center metal, is stabilized, and the olefin-based monomer can approach only at a specific position. Therefore, the transition metal compounds for the olefin polymerization catalysts of chemical formulas A and B have high activity as a catalyst, and may form a region having a high electron density between the catalyst center metals by non-bonding electron pairs of hetero atoms. Due to this, when the olefin monomer approaches, it may have a structure that induces a specific approach to only a region having a small steric effect, and the prepared olefin polymer may have a steric specific structure.

Although the embodiments of the present invention have been described above, the present invention is not limited to the above embodiments, and may be prepared in various different forms, and those skilled in the art to which the present invention pertains will understand that other specific forms may be practiced without changing the technical spirit or essential features of the present invention. Therefore, it should be understood that the embodiments described above are illustrative in all respects and not restrictive.

What is claimed is:

1. A transition metal compound for an olefin polymerization catalyst represented by the following chemical formula 1:

<chemical formula 1>

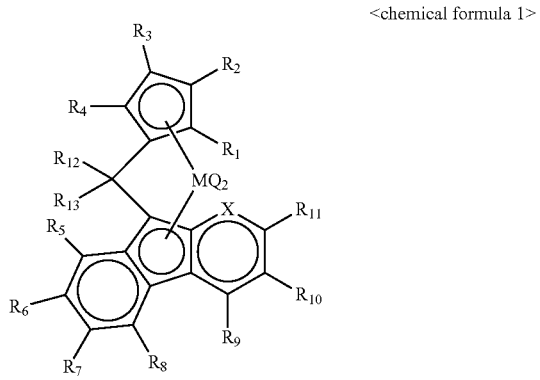

In chemical formula 1,

M is titanium (Ti), zirconium (Zr) or hafnium (Hf),

Q is each independently halogen, a $C_{1-20}$ alkyl group, a $C_{2-20}$ alkenyl group, a $C_{2-20}$ alkynyl group, a $C_{6-20}$ aryl group, a $C_{1-20}$ alkyl $C_{6-20}$ aryl group, a $C_{6-20}$ aryl $C_{1-20}$ alkyl group, a $C_{1-20}$ alkylamido group, a $C_{6-20}$ arylamido group or a $C_{1-20}$ alkylidene group, X is nitrogen (N) or phosphorus (P), $R_1$, $R_2$, $R_3$, $R_4$, $R_5$, $R_6$, $R_7$, $R_8$, $R_9$, $R_{10}$ and $R_{11}$ are each independently hydrogen, a $C_{1-20}$ alkyl group, a $C_{2-20}$ alkenyl group, a $C_{2-20}$ alkynyl group, a $C_{6-20}$ aryl group, a $C_{1-20}$ alkyl $C_{6-20}$ aryl group, a $C_{6-20}$ aryl $C_{1-20}$ alkyl group, a $C_{1-20}$ alkylamido group, a $C_{6-20}$ arylamido group or a $C_{1-20}$ alkylidene group, $R_{12}$ and $R_{13}$ are each independently a $C_{1-20}$ alkyl group, a $C_{2-20}$ alkenyl group, a $C_{2-20}$ alkynyl group, a $C_{6-20}$ aryl group, a $C_{1-20}$ alkyl $C_{6-20}$ aryl group, a $C_{6-20}$ aryl $C_{1-20}$ alkyl group, a $C_{1-20}$ alkylamido group, a $C_{6-20}$ arylamido group or a $C_{1-20}$ alkylidene group, or are linked to each other to form a substituted or unsubstituted $C_{4-20}$ ring.

2. The transition metal compound of claim 1, wherein Q is each independently halogen or a $C_{1-20}$ alkylamido group, wherein $R_1$, $R_2$, $R_3$ and $R_4$ are each independently hydrogen, wherein $R_5$, $R_6$, $R_7$, $R_8$, $R_9$, $R_{10}$ and $R_{11}$ are each independently hydrogen, a $C_{1-20}$ alkyl group, a phenyl group or a t-butyl group, wherein $R_{12}$ and $R_{13}$ are each independently phenyl group or a $C_{1-20}$ alkyl group, or linked to each other to form a substituted or unsubstituted $C_{4-20}$ ring.

3. The transition metal compound of claim 2, wherein $R_{12}$ and $R_{13}$ are each independently a phenyl group or a methyl group or linked to each other to form an aliphatic $C_{4-6}$ ring.

4. The transition metal compound of claim 2,
wherein $R_5$, $R_6$, $R_7$, $R_8$, $R_9$, $R_{10}$ and $R_{11}$ are each independently hydrogen, a phenyl group, a methyl group or a t-butyl group.

5. The transition metal compound of claim 3,
wherein chemical formula 1 is selected from chemical formulas 1-1 to 1-23:

<chemical formula 1-1>

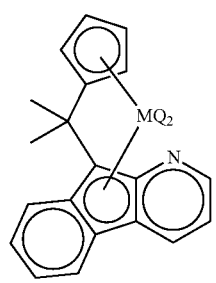

<chemical formula 1-2>

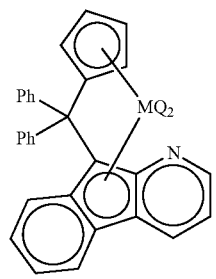

<chemical formula 1-3>

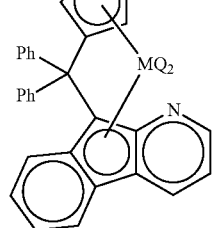

<chemical formula 1-4>

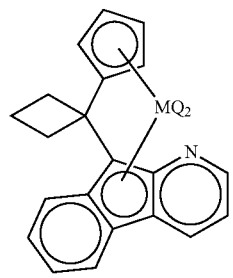

<chemical formula 1-5>

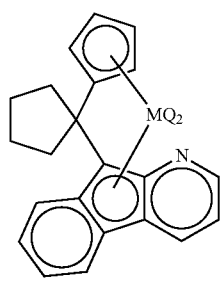

<chemical formula 1-6>

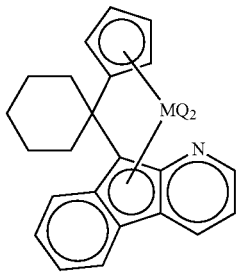

<chemical formula 1-7>

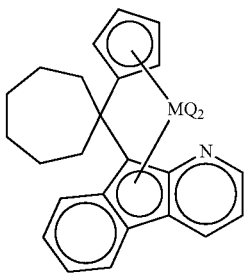

<chemical formula 1-8>

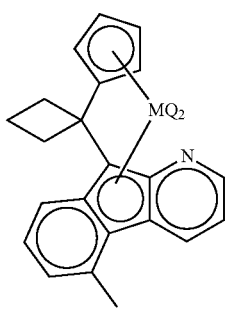

<chemical formula 1-9>

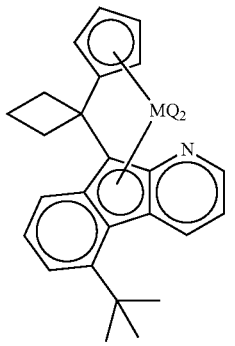

<chemical formula 1-10>

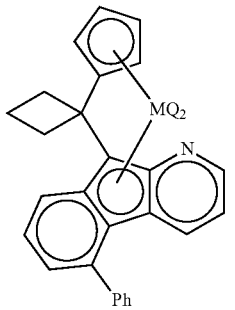

<chemical formula 1-11>
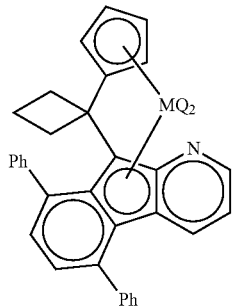
<chemical formula 1-12>
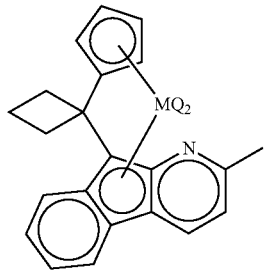
<chemical formula 1-13>
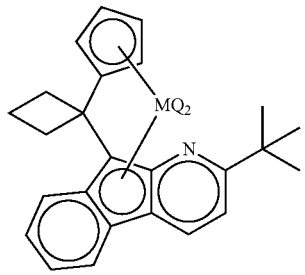
<chemical formula 1-14>
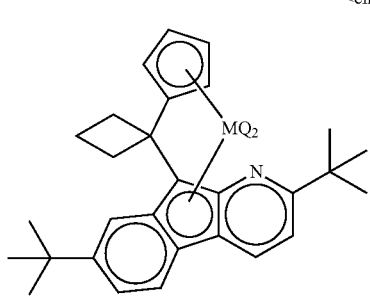
<chemical formula 1-15>
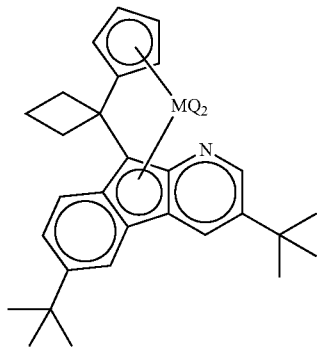
<chemical formula 1-16>
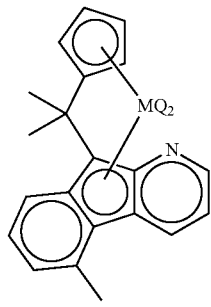
<chemical formula 1-17>
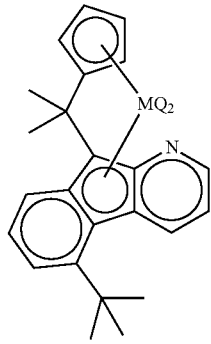
<chemical formula 1-18>
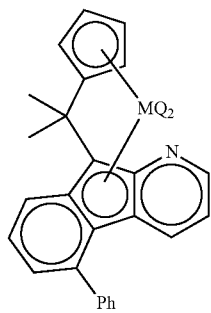
<chemical formula 1-19>
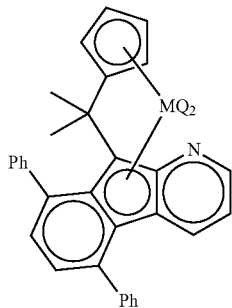
<chemical formula 1-20>
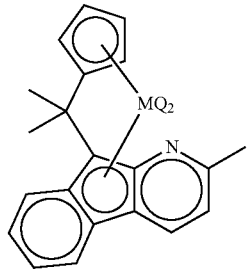

<chemical formula 1-21>

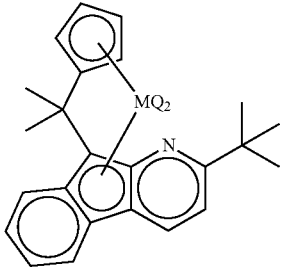

<chemical formula 1-22>

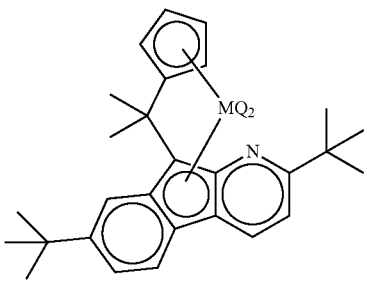

<chemical formula 1-23>

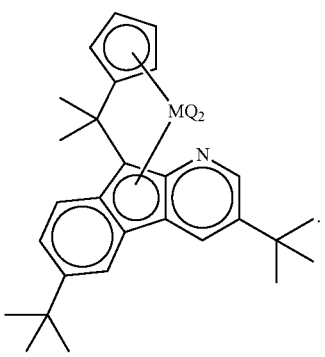

6. An olefin polymerization catalyst comprising:

a transition metal compound for an olefin polymerization catalyst represented by the following chemical formula 1; and a cocatalyst compound, <chemical formula 1>

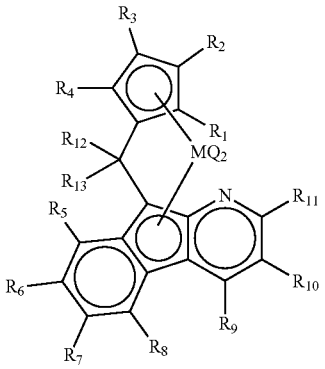

In the chemical formula 1,

M is any one of titanium (Ti), zirconium (Zr) and hafnium (Hf),

Q is each independently halogen, a $C_{1-20}$ alkyl group, a $C_{2-20}$ alkenyl group, a $C_{2-20}$ alkynyl group, a $C_{6-20}$ aryl group, a $C_{1-20}$ alkyl $C_{6-20}$ aryl group, a $C_{6-20}$ aryl $C_{1-20}$ alkyl group, a $C_{1-20}$ alkylamido group, a $C_{6-20}$ arylamido group or a $C_{1-20}$ alkylidene group, X is nitrogen (N) or phosphorus (P), $R_1$, $R_2$, $R_3$, $R_4$, $R_5$, $R_6$, $R_7$, $R_8$, $R_9$, $R_{10}$ and $R_{11}$ are each independently hydrogen, a $C_{1-20}$ alkyl group, a $C_{2-20}$ alkenyl group, a $C_{2-20}$ alkynyl group, a $C_{6-20}$ aryl group, a $C_{1-20}$ alkyl $C_{6-20}$ aryl group, a $C_{6-20}$ aryl $C_{1-20}$ alkyl group, a $C_{1-20}$ alkylamido group, a $C_{6-20}$ arylamido group or a $C_{1-20}$ alkylidene group, $R_{12}$ and $R_{13}$ are each independently a $C_{1-20}$ alkyl group, a $C_{2-20}$ alkenyl group, a $C_{2-20}$ alkynyl group, a $C_{6-20}$ aryl group, a $C_{1-20}$ alkyl $C_{6-20}$ aryl group, a $C_{6-20}$ aryl $C_{1-20}$ alkyl group, a $C_{1-20}$ alkylamido group, a $C_{6-20}$ arylamido group or a $C_{1-20}$ alkylidene group, or are linked to each other to form a substituted or unsubstituted $C_{4-20}$ ring.

7. The olefin polymerization catalyst of claim 6, wherein the cocatalyst compound comprises at least any one of compounds represented by the following chemical structure formulas 2 to 4:

<chemical formula 2>

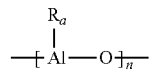

In the chemical formula 2, n is an integer of 2 or more, $R_a$ is a halogen atom, a $C_{1-20}$ hydrocarbon group or a $C_{1-20}$ hydrocarbon group substituted with halogen, <chemical formula 3>

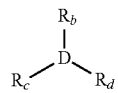

In the chemical formula 3,

D is aluminum (Al) or boron (B), $R_b$, $R_c$ and $R_d$ are each independently a halogen atom, a $C_{1-20}$ hydrocarbon group, a $C_{1-20}$ hydrocarbon group substituted with halogen, or a $C_{1-20}$ alkoxy group, $[L-H]^+[Z(A)_4]^-$ or $[L]^+[Z(A)_4]^-$    <chemical formula 4>

In the chemical formula 4,

L is a neutral or cationic Lewis base, $[L-H]^+$ and $[L]^+$ are Brønsted acids, Z is a group 13 element, A is each independently a substituted or unsubstituted $C_{6-20}$ aryl group or a substituted or unsubstituted $C_{1-20}$ alkyl group.

8. The olefin polymerization catalyst of claim 6, wherein Q is each independently halogen or a $C_{1-20}$ alkylamido group, wherein $R_1$, $R_2$, $R_3$ and $R_4$ are each independently hydrogen, wherein $R_5$, $R_6$, $R_7$, $R_8$, $R_9$, $R_{10}$ and $R_{11}$ are each independently hydrogen, a $C_{1-20}$ alkyl group, a phenyl group or a t-butyl group, wherein the $R_{12}$ and $R_{13}$ are each independently a phenyl group or a $C_{1-20}$ alkyl group, or are linked to each other to form a substituted or unsubstituted $C_{4-20}$ ring.

9. The olefin polymerization catalyst of claim 8, wherein $R_{12}$ and $R_{13}$ are each independently a phenyl group or a methyl group or linked to each other to form an aliphatic $C_{4-6}$ ring.

10. The olefin polymerization catalyst of claim 8, wherein $R_5$, $R_6$, $R_7$, $R_8$, $R_9$, $R_{10}$ and $R_{11}$ are each independently hydrogen, a phenyl group, a methyl group or a t-butyl group.

11. The olefin polymerization catalyst of claim 9, wherein the chemical formula 1 is selected from the following chemical formulas 1-1 to 1-23:

<chemical formula 1-1>

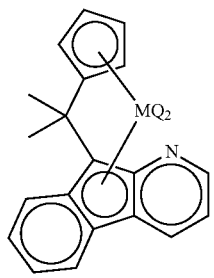

<chemical formula 1-2>

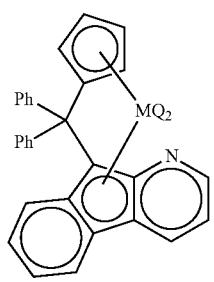

<chemical formula 1-3>

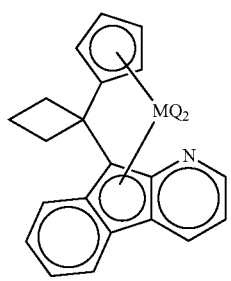

<chemical formula 1-4>

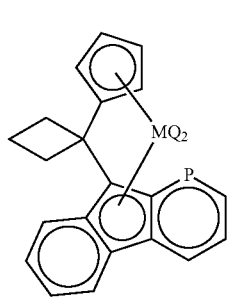

<chemical formula 1-5>

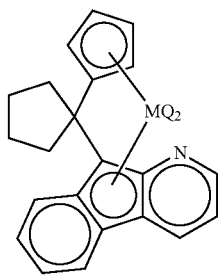

<chemical formula 1-6>

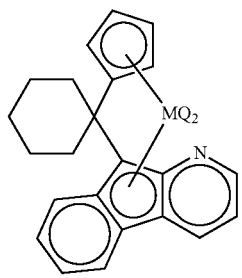

<chemical formula 1-7>

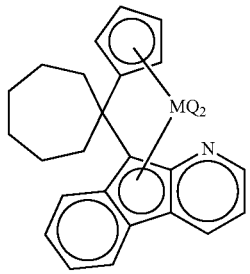

<chemical formula 1-8>

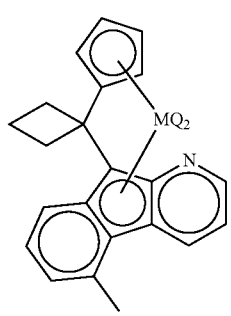

<chemical formula 1-9>

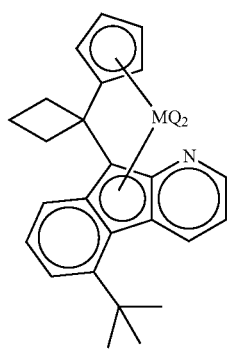

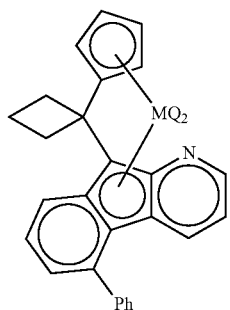
<chemical formula 1-10>
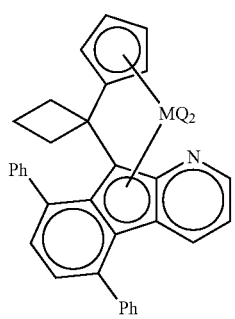
<chemical formula 1-11>
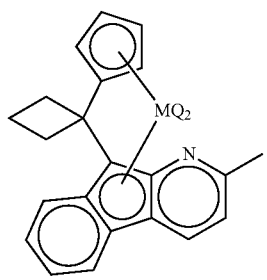
<chemical formula 1-12>
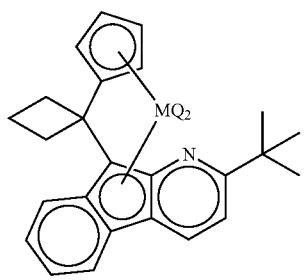
<chemical formula 1-13>
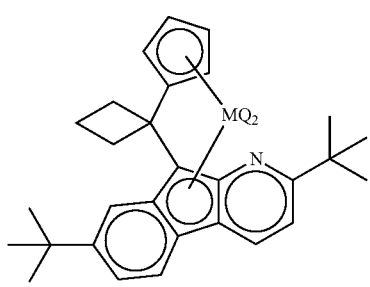
<chemical formula 1-14>
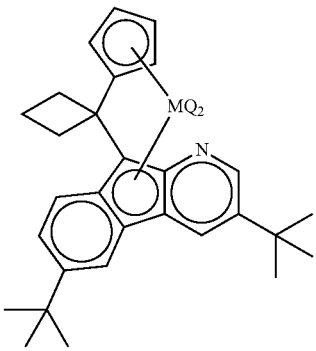
<chemical formula 1-15>
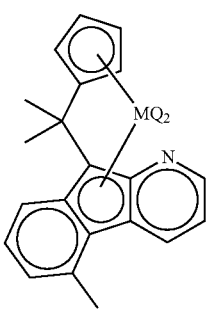
<chemical formula 1-16>
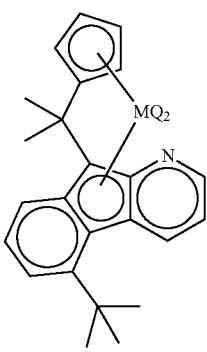
<chemical formula 1-17>
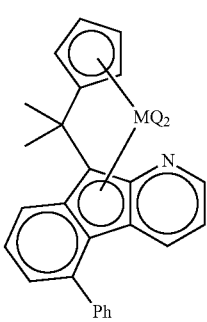
<chemical formula 1-18>
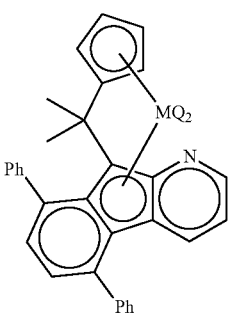
<chemical formula 1-19>

-continued
<chemical formula 1-20>
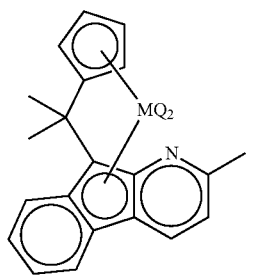
<chemical formula 1-21>
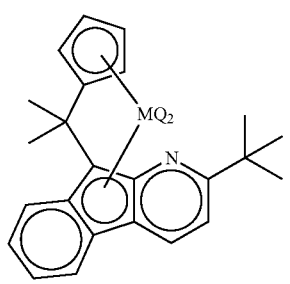
<chemical formula 1-22>
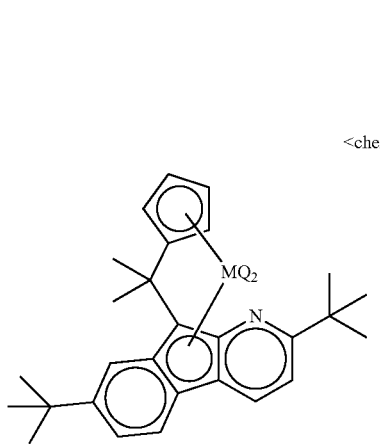
<chemical formula 1-23>
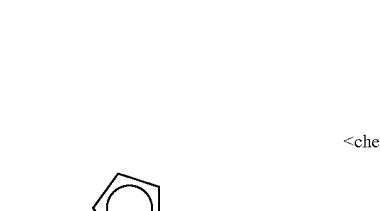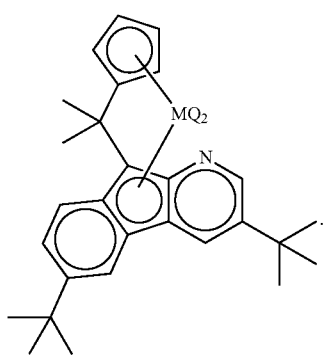
12. The transition metal compound of claim 4, wherein the chemical formula 1 is selected from the following chemical formulas 1-1 to 1-23:
<chemical formula 1-1>
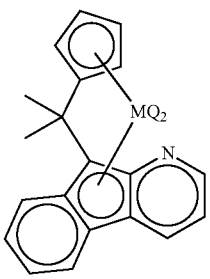
<chemical formula 1-2>
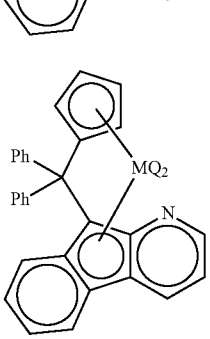
<chemical formula 1-3>
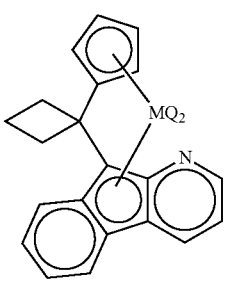
<chemical formula 1-4>
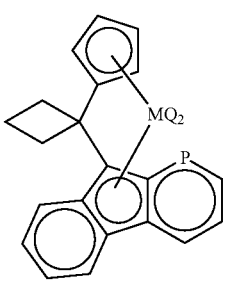
<chemical formula 1-5>
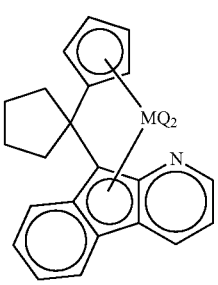

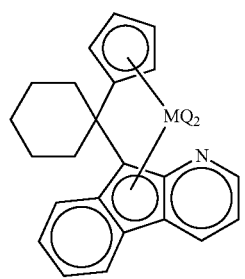
<chemical formula 1-6>
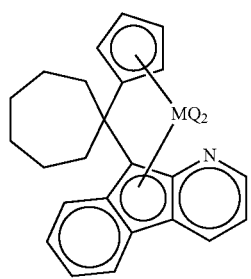
<chemical formula 1-7>
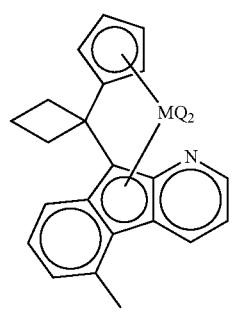
<chemical formula 1-8>
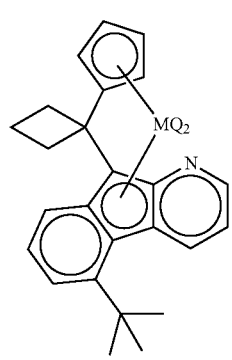
<chemical formula 1-9>
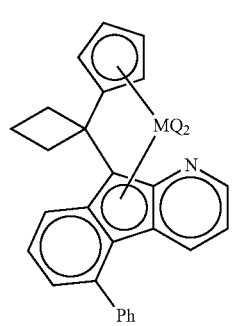
<chemical formula 1-10>
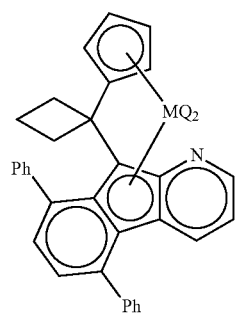
<chemical formula 1-11>
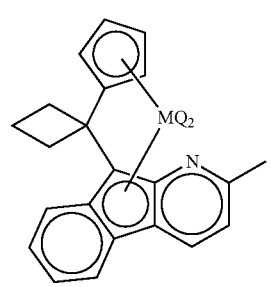
<chemical formula 1-12>
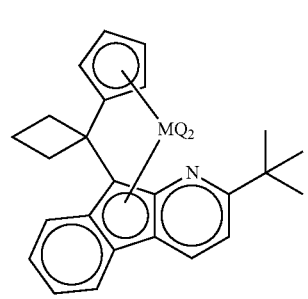
<chemical formula 1-13>
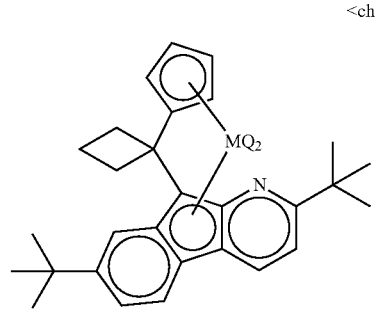
<chemical formula 1-14>
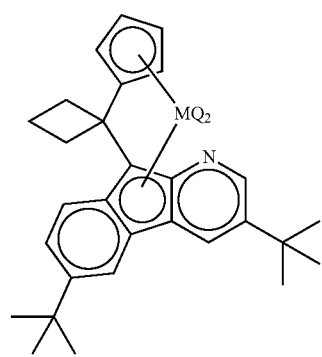
<chemical formula 1-15>

<chemical formula 1-16>
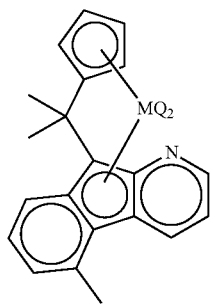
<chemical formula 1-17>
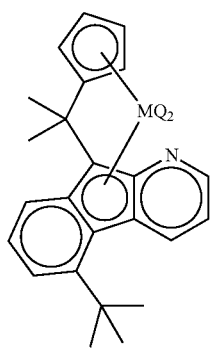
<chemical formula 1-18>
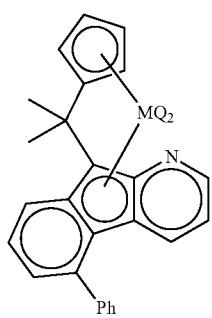
<chemical formula 1-19>
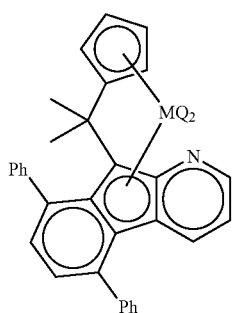
<chemical formula 1-20>
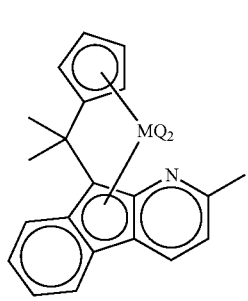
<chemical formula 1-21>
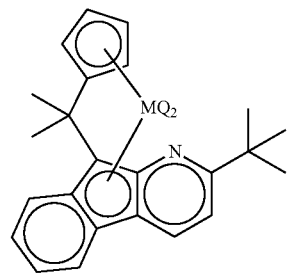
<chemical formula 1-22>
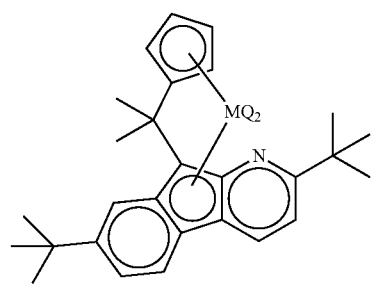
<chemical formula 1-23>
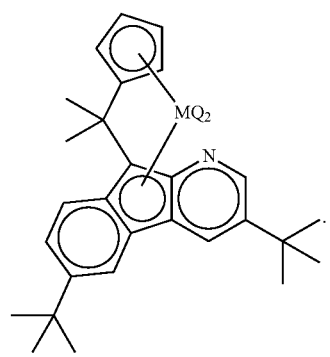
13. The olefin polymerization catalyst of claim 10, wherein the chemical formula 1 is selected from the following chemical formulas 1-1 to 1-23:
<chemical formula 1-1>
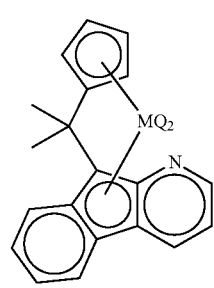

<chemical formula 1-2>
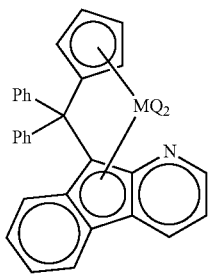
<chemical formula 1-3>
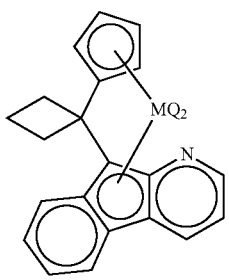
<chemical formula 1-4>
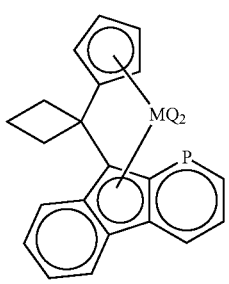
<chemical formula 1-5>
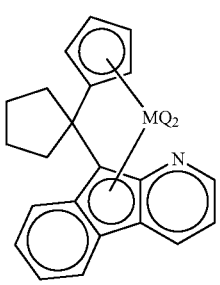
<chemical formula 1-6>
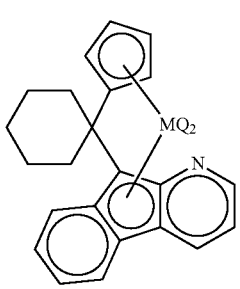
<chemical formula 1-7>
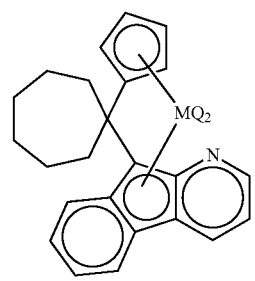
<chemical formula 1-8>
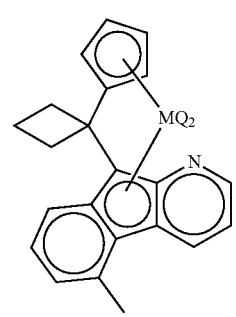
<chemical formula 1-9>
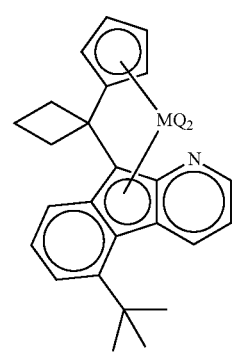
<chemical formula 1-10>
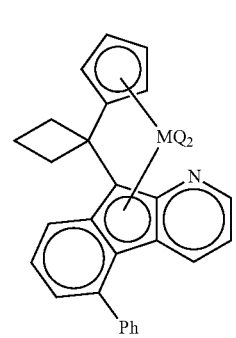
<chemical formula 1-11>
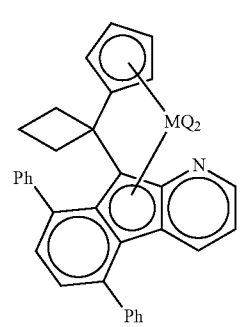

<chemical formula 1-12>
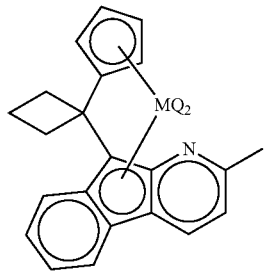
<chemical formula 1-13>
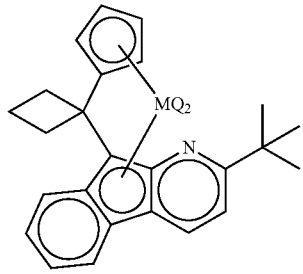
<chemical formula 1-14>
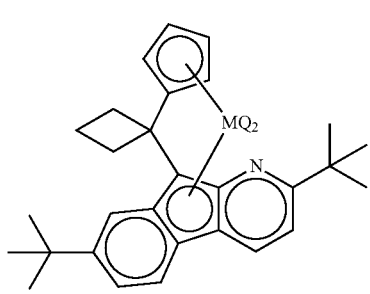
<chemical formula 1-15>
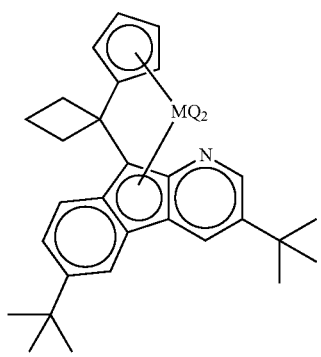
<chemical formula 1-16>
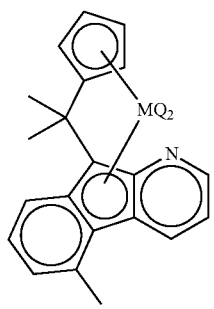
<chemical formula 1-17>
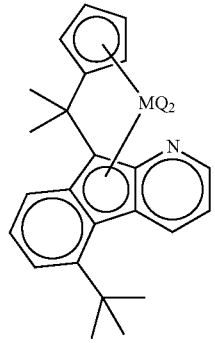
<chemical formula 1-18>
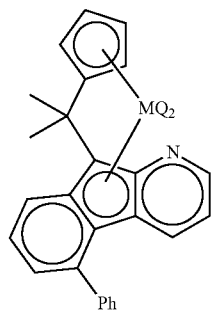
<chemical formula 1-19>
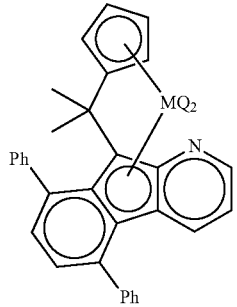
<chemical formula 1-20>
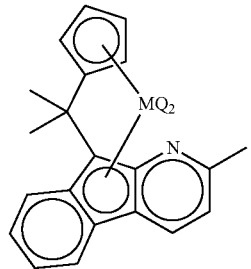
<chemical formula 1-21>
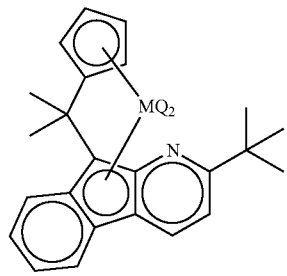

-continued
<chemical formula 1-22>
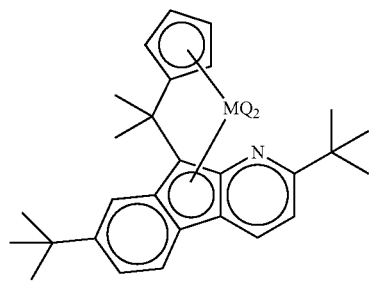
<chemical formula 1-23>
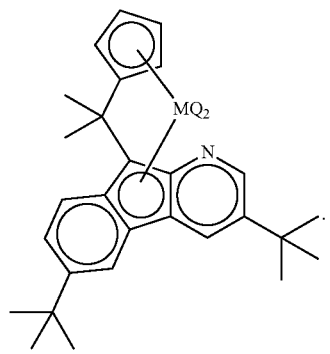
* * * * *